(12) United States Patent
Gong et al.

(10) Patent No.: US 10,913,909 B2
(45) Date of Patent: Feb. 9, 2021

(54) SELECTION OF BRIGHT STOCK PROCESSING CONDITIONS BASED ON SAMPLE CHARACTERIZATION

(71) Applicant: ExxonMobil Research and Engineering Company, Annandale, NJ (US)

(72) Inventors: Liezhong Gong, Basking Ridge, NJ (US); Helen S. Wellons, Annandale, NJ (US); Kuangnan Qian, Skillman, NJ (US); Lisa I. Yeh, Marlton, NJ (US); James W. Gleeson, Magnolia, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/706,992

(22) Filed: Dec. 9, 2019

(65) Prior Publication Data
US 2020/0190415 A1 Jun. 18, 2020

Related U.S. Application Data

(60) Provisional application No. 62/781,281, filed on Dec. 18, 2018.

(51) Int. Cl.
*C10G 73/34* (2006.01)
*C10G 73/04* (2006.01)
*C10G 73/06* (2006.01)

(52) U.S. Cl.
CPC .............. *C10G 73/34* (2013.01); *C10G 73/04* (2013.01); *C10G 73/06* (2013.01); *C10G 2300/1077* (2013.01); *C10G 2300/302* (2013.01); *C10G 2300/304* (2013.01); *C10G 2400/10* (2013.01)

(58) Field of Classification Search
CPC ........ C10G 73/34; C10G 73/04; C10G 73/06; C10G 73/02; C10G 73/36; C10G 2300/1077; C10G 2300/302; C10G 2300/304; C10G 21/003; C10G 45/58; H01J 49/38; G01N 33/2823
See application file for complete search history.

(56) References Cited

U.S. PATENT DOCUMENTS

| | | | | |
|---|---|---|---|---|
| 3,458,432 | A | * | 7/1969 | Barron .................. C10G 73/34 208/36 |
| 4,885,062 | A | * | 12/1989 | Harrison ............... C10G 73/34 196/14.5 |
| 8,452,548 | B2 | | 5/2013 | Gould et al. |
| 8,992,770 | B2 | * | 3/2015 | Gong ................. G01N 33/2823 208/291 |
| 2007/0114377 | A1 | * | 5/2007 | Qian .................. G01N 30/7206 250/282 |
| 2015/0041634 | A1 | * | 2/2015 | Quann .................. C10G 45/10 250/282 |
| 2017/0183578 | A1 | * | 6/2017 | Hilbert ............... C10G 67/0481 |

FOREIGN PATENT DOCUMENTS

WO WO-2016111988 A1 * 7/2016 ......... G01N 33/2823

OTHER PUBLICATIONS

Pillon, "Surface Activity of Petroleum Derived Lubricants" (2011), CRC Press, p. 27.
Garner, et al., "OTC 22660 Analysis and Comparison of Paraffinic Field Deposits to Cold Finger Deposits on a Brazilian Campos Basin Crude Oil", (2011), Offshore Technology Conference, vol. 2, pp. 1078-1093.
Dai, et al., "Influence of Resins on Crystallization and Gelation of Waxy Oils", Energy & Fuels, vol. 33, No. 1, Dec. 11, 2018, pp. 185-196.
The International Search Report and Written Opinion of PCT/US2019-065133 dated Apr. 30, 2020.

* cited by examiner

*Primary Examiner* — Michelle Stein
(74) *Attorney, Agent, or Firm* — Scott F. Yarnell

(57) ABSTRACT

Systems and methods are provided for modifying or selecting processing conditions for bright stock formation based on compositional characterization of the feedstock and/or bright stock products. In some aspects, the compositional information can include Z-class characterization of the components of a feed and/or bright stock product, optionally in combination with carbon number and/or molecular weight for the components. The compositional information can be used to select processing conditions to allow for removal and/or modification of selected components within a bright stock in order to improve throughput and/or provide desirable cold flow properties.

18 Claims, 10 Drawing Sheets

SELECTION OF BRIGHT STOCK PROCESSING CONDITIONS BASED ON SAMPLE CHARACTERIZATION

CROSS-REFERENCE TO RELATED APPLICATIONS

This application claims priority to U.S. Provisional Application Ser. No. 62/781,281 filed Dec. 18, 2018, which is herein incorporated by reference in its entirety.

FIELD

Systems and methods are provided for production of bright stocks by selecting processing conditions based on compositional characterization.

BACKGROUND

Bright stock is a type of base stock with high viscosity (e.g., kinematic viscosity at 100° C.>25 cSt) typically obtained from vacuum residues of petroleum distillation. Dewaxing, namely the removal of waxy species using either solvents or catalysts, is an important step in manufacturing bright stock to ensure the resulting bright stock has the desired low temperature properties.

Finished lubricant performance is significantly impacted by base oil parameters and composition. Various performance parameters for finished lubricants are related to low temperature properties, i.e., the viscosities a finished lubricant possesses in various shear environments for different product applications. These viscosities are often affected by both the nature of the test employed and the relatively low concentration of residual waxy components in the base oils used to create the formulation. This is because the presence of residual wax in base oils can lead to a high pour point and negatively impact the low temperature properties of base oils. Such effects are caused by crystallization of waxy molecules at low temperatures, resulting in turbidity and an increase in viscosity.

U.S. Pat. No. 8,452,548 describes using residual wax contents as measured by differential scanning calorimetry (DSC) to predict low temperature performance for base stocks.

U.S. Patent Application Publication 2015/0041634 describes use of Fourier Transform Ion Cyclotron Resonance (FTICR) mass spectrometry for characterization of kerosene fractions and prediction of whether a kerosene sample can satisfy a thermal breakpoint specification. The methods include constructing a model based on a library of FTICR characterizations with corresponding bulk property measurements, and then correlating bulk property measurements for an unknown sample to determine an expected FTICR profile, which can then be used to make predictions regarding the kerosene sample.

SUMMARY

In various aspects, a method for forming a bright stock is provided. The method includes performing FTICR on a sample of a feedstock to determine amounts of one or more Z-classes within the feedstock, to determine amounts of one or more homologous series of compounds within the feedstock, or a combination thereof. The method can further include characterizing waxy components within the sample of the feedstock based on the one or more determined Z-classes, the determined one or more homologous series of compounds, or the combination thereof. The method can further include selecting at least one processing condition based on the characterization of the waxy components. Optionally, the at least one processing condition can correspond to at least one of a pour point, a feed rate, a dewaxing temperature, a solvent to oil ratio, and a dewaxing solvent. The method can further include performing solvent dewaxing and/or catalytic dewaxing. In aspects corresponding to solvent dewaxing, the method can further include performing solvent dewaxing on at least a portion of the feedstock under solvent dewaxing conditions to form a dewaxed oil, the dewaxed oil comprising a bright stock portion having a kinematic viscosity at 100° C. of 20 cSt or more, the solvent dewaxing conditions comprising the at least one of the pour point, the feed rate, the dewaxing temperature, the solvent to oil ratio, and the dewaxing solvent. In aspects corresponding to catalytic dewaxing, the method can include performing catalytic dewaxing on at least a portion of the feedstock under catalytic dewaxing conditions to form a dewaxed oil, the catalytic dewaxing conditions comprising the at least one processing condition, the dewaxed oil comprising a bright stock portion having a kinematic viscosity at 100° C. of 20 cSt or more.

In some alternative aspects, the solvent processing characterized using FTICR can correspond to de-oiling of a wax product formed by a solvent dewaxing process.

DETAILED DESCRIPTION

Figure 1:
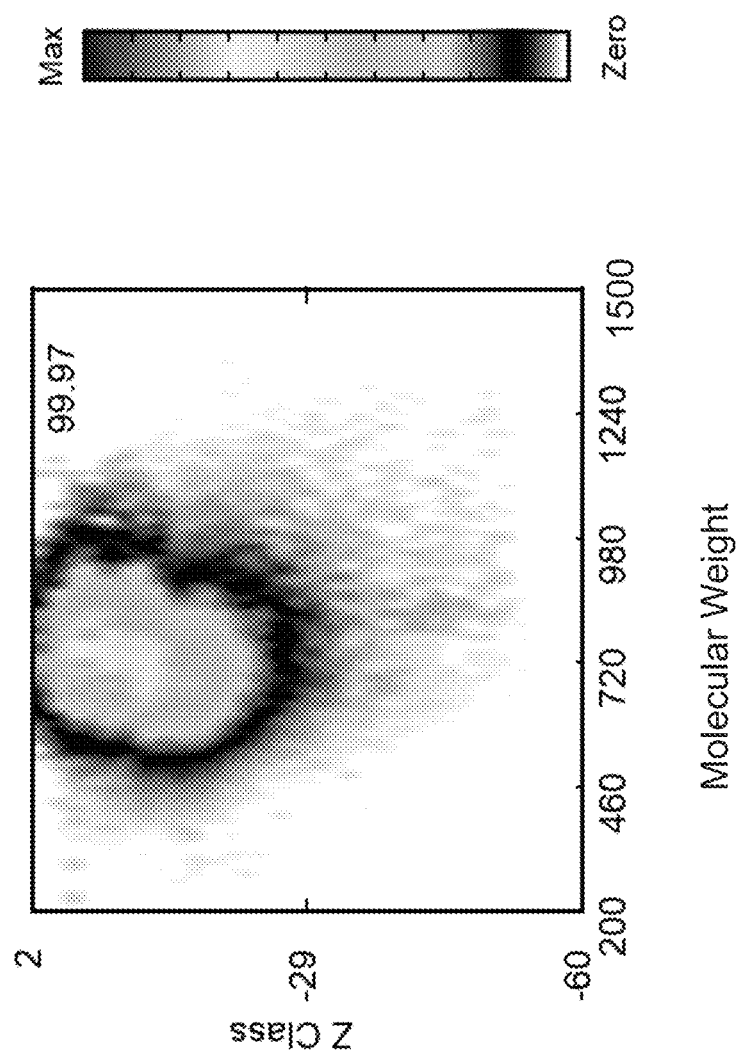
FIG. 1 shows an FTICR characterization of the composition of a raffinate feed for bright stock production.

All numerical values within the detailed description and the claims herein are modified by "about" or "approximately" the indicated value, and take into account experimental error and variations that would be expected by a person having ordinary skill in the art.

Overview

In various aspects, systems and methods are provided for modifying or selecting processing conditions for bright stock formation based on compositional characterization of the feedstock and/or bright stock products. In some aspects, the compositional information can include Z-class characterization of the components of a feed and/or bright stock product, optionally in combination with carbon number and/or molecular weight for the components. The compositional information can be used to select processing conditions to allow for removal and/or modification of selected components within a bright stock in order to improve throughput and/or provide desirable cold flow properties. For example, the wax or paraffin content of a feedstock can be characterized to determine the nature of the wax components present in the feed. The wax characterization information can then be used to select processing conditions that can be effective for achieving one or more target properties, such as selection of processing conditions suitable for removal of wax components that are not compatible with a desired or target pour point for the resulting bright stock.

It has been discovered that the wax content in bright stock and/or feeds for bright stock production is qualitatively different from the wax content in a corresponding heavy neutral base stock and/or feed for heavy neutral base stock production. These compositional differences can potentially require different processing considerations in order to produce a lubricant stock having a desired set of properties. By using an analytical method such as Fourier-Transform Ion Cyclotron Resonance (FTICR) mass spectrometry, such compositional features can be identified in both the feedstock and the composition. This can allow for determination of compositional features that impact cold flow properties and/or processing conditions.

Conventionally, selection of processing conditions to produce a bright stock with desirable properties has been performed largely on a trial-and-error basis. While this can be effective in some instances, it can lead to use of higher severity processing conditions than necessary, in order to ensure that desired properties are achieved. This can result in loss of yield and/or other processing inefficiencies.

In contrast to conventional methods, performing detailed compositional characterization of the types of components within a bright stock feed can allow for selection of processing conditions that are tailored to the production of a desired bright stock product from a given feed. For example, in some aspects, this can correspond to selecting processing conditions in order to achieve a desired cold flow property, such as achieving a desired pour point. In other aspects, this can correspond to selecting processing conditions that are sufficient to remove a desired amount of a particular compositional component. This can include selecting processing conditions to achieve a target compositional feature in the resulting bright stock product, such as processing conditions to achieve a desired level of residual wax. Another option can be to use the FTICR information to determine dewaxing conditions that are sufficient to reduce the concentration of one or more components within a feedstock to a level that is correlated with a desired pour point. The one or more components can correspond to for example, components having a specified combination of Z-class and molecular weight range (or alternatively Z-class and carbon number), or components within one or more homologous series of compounds, or components specified in another convenient manner based on the FTICR data. In still other aspects, this can correspond to selecting processing conditions that provide improved process stability. For example, for a solvent dewaxing process, a size for the filter cake during solvent dewaxing that is based on the amount and types of waxy components present in a feed can be selected. For a catalytic dewaxing process, the dewaxing conditions can be selected to provide a sufficient severity. In yet other aspects, this can correspond to using compositional information to determine an appropriate feedstock for formation of bright stock.

The above characterization values are complemented in the library by a second type of characterization of samples, which is performed using Fourier-Transform Ion Cyclotron Resonance mass spectroscopy (FTICR). Using FTICR, individual compounds within a bright stock feed sample and/or resulting dewaxing product sample can be identified both in terms of composition and quantity. This allows for a detailed qualitative and quantitative understanding of the types of molecules present in a bright stock feed and/or product sample. It is noted that solvent dewaxing generates both a dewaxed oil product and a wax product that can be characterized, with the dewaxed oil corresponding to a bright stock product while the wax product includes compounds removed from the feed by the dewaxing process. By contrast, catalytic dewaxing generates a single effluent. Optionally, the catalytic dewaxing effluent can be fractionated (if needed) to form a bright stock product prior to performing characterization. Based on the detailed information about the compounds within a feed and/or product sample, the compounds can be organized into compositional groups.

The bulk physical properties for a brightstock feed and/or product, such as pour point, cloud point, paraffin content, sulfur content, or other readily characterized values for a brighstock feed sample and/or product sample can also potentially be used as part of the characterization. In some aspects, the characterization of physical properties can be limited to properties that are readily obtained in a non-laboratory setting, such as a refinery setting. Examples of readily obtained properties in a refinery setting include sulfur content, nitrogen content, pour point, cloud point, paraffin content, and wax content. Optionally, such readily obtained bulk properties can also be used for in conjunction with FTICR data for an individual sample when determining or modifying dewaxing conditions.

In some optional aspects, in order to predict the cold flow properties of a bright stock product and/or predict dewaxing conditions that will result in a dewaxed bright stock sample that achieves one or more desired cold flow properties, a library of data containing reference bright stock samples can be acquired using a variety of characterization methods. The data for the reference bright stock samples can be based on measurements performed on bright stock feeds and/or product fractions from a plurality of crude sources. Alternatively, a library can be constructed of reference bright stock samples derived from a single crude source for use in predicting properties of a specific type of bright stock fraction.

One option for using compositional information to characterize a feed or product sample (and/or to construct a model for predicting dewaxing conditions) is to use a convenient definition for the compositional groups when analyzing FTICR data. For example, one way to define compositional groups is based on a "Z-class" for the compositional groups. The Z-class is a number based on the concept that the basic ratio of carbon to hydrogen in a hydrocarbon is one carbon per two hydrogens. The Z-class represents the deviation of the ratio of carbon to hydrogen in a compound. For example, an alkane has a Z-class of +2, since an alkane has a basic formula of $C_nH_{2n+2}$. A compound with one degree of unsaturation and/or one closed ring structure, such as an alkene or a single ring cycloalkane, has a Z-class of zero. As more degrees of unsaturation and/or additional rings are included in a compound, the Z-class will continue to decrease. For example, benzene has a Z-class of −6, corresponding to one ring structure plus three degrees of unsaturation. It is noted that the presence of heteroatoms may also contribute to the Z-class of a compound. Selecting compositional groups based on the Z-class of a compound can allow for a more refined model while still limiting the characterization (or limiting the model) to a manageable amount of data. It is noted that the Z-class of a compound can alternatively be referred to as the Z-class number or the Z number.

Another option can be to characterize one or more series of homologous compounds within a composition. Characterizing a homologous series can be beneficial, for example, for determining how the compounds within the series are impacted by dewaxing. In the case of solvent dewaxing, this can include characterizing the split of each component in a homolog series between the dewaxed oil and the wax product.

In some aspects, the detailed information from FTICR can be combined with the physical property measurements to determine a correlation. Although FTICR provides more detailed information, the nature of FTICR makes the technique difficult to incorporate into a refinery (or other non-laboratory) setting. Instead, the FTICR information can be used to construct a model for evaluating bright stock feeds and/or product fractions based on values that are more readily obtained, pour point, kinematic viscosity, and other bulk compositional/physical properties. Additionally or alternatively, the FTICR information can be used to determine compositional information for a dewaxed product based on a combination of feedstock and processing conditions, so that modifications to the processing conditions can be determined to achieve a compositional profile in the product that correlates with a desired cold flow property, such as a desired pour point. In such an aspect, the FTICR information can be used to determine and/or modify processing conditions corresponding to solvent dewaxing conditions or corresponding to catalytic dewaxing conditions.

As an example, one type of prediction that can be made based on FTICR information is a prediction of wax yield from a potential raffinate feed during solvent dewaxing. FTICR information can be used to determine the relative amounts of various homologous series of compounds within a raffinate feed sample. A compositional correlation or model can then be used to determine how each individual homologous series, at a specific dewaxing temperature, will split between the dewaxed oil phase and the wax phase. A predicted wax yield can then be determined by summing the amount of wax that ends up in the wax phase for each homologous series, and dividing that value by the total mass of the feed to the solvent dewaxing process.

Another variation on the above example is the ability to predict the residual wax at a given temperature within a dewaxed oil produced from solvent dewaxing. Using the characterization of the homologous series within a raffinate feed, the residual wax within a dewaxed oil sample can be determined. For example, a dewaxed oil corresponding to a bright stock can be formed by dewaxing at a dewaxing temperature, such as −6° C. It may be desirable to determine the residual wax in the dewaxed oil relative to a second temperature, such as −15° C. Using the homologous series information, the wax yield at −15° C. and the wax yield at −6° C. for the feedstock can be calculated. The residual wax at −15° C. for the dewaxed oil formed at −6° C. can then be predicted by subtracting the calculated wax yield at −6° C. from the calculated wax yield at −15° C.

Feedstocks

A wide range of petroleum and chemical feedstocks can be used to form lubricant base stocks, such as bright stocks. Suitable feedstocks include whole and reduced petroleum crudes, atmospheric, cycle oils, gas oils, including vacuum gas oils and coker gas oils, light to heavy distillates including raw virgin distillates, hydrocrackates, hydrotreated oils, slack waxes, Fischer-Tropsch waxes, raffinates, deasphalted oils, and mixtures of these materials.

The feedstock can optionally include desasphalted oil. In some aspects, a deasphalted oil can correspond to a low lift deasphalted oil, such as a deasphalted oil formed by deasphalting a vacuum resid boiling range feed (T10 distillation point of 510° C. or more) to produce a yield of deasphalted oil of roughly 40 wt % or less, or 35 wt % or less, or 30 wt % or less, such as down to 20 wt % or possibly still lower. This can correspond to, for example, a deasphalted oil formed by conventional propane deasphalting of a vacuum resid boiling range feed. In other aspects, a deasphalted oil can correspond to a high lift deasphalted oil, such as a deasphalted oil formed by deasphalting a vacuum resid boiling range feed (T10 distillation point of 510° C. or more) to produce a yield of deasphalted oil of at least 50 wt %, or at least 60 wt %, or at least 65 wt %, or at least 70 wt % such as up to 80 wt % or possibly still higher. This can correspond to, for example, a deasphalted oil formed by deasphalting using a $C_{4+}$ solvent or a $C_{5+}$ solvent. A $C_{n+}$ solvent is defined as a hydrocarbon solvent that includes at least 50 wt % of alkanes that contain "n" carbons or more, or at least 75 wt %, such as up to the solvent being substantially completely composed of alkanes that contain "n" carbons or more. Butane is an example of a $C_4$ solvent. Pentane, hexane, and heptane are examples of $C_{5+}$ solvents. It is noted that alkanes can include n-alkanes and branched alkanes.

One way of defining a feedstock is based on the boiling range of the feed. One option for defining a boiling range is to use an initial boiling point for a feed and/or a final boiling point for a feed. Another option is to characterize a feed based on the amount of the feed that boils at one or more temperatures. For example, a "T5" boiling point/distillation point for a feed is defined as the temperature at which 5 wt % of the feed will boil off. Similarly, a "T95" boiling point/distillation point is a temperature at 95 wt % of the feed will boil. Boiling points, including fractional weight boiling points, can be determined using a suitable ASTM method, such as ASTM D2887. In the event that ASTM D2887 is not suitable, ASTM D7169 can be used instead.

Typical feeds include, for example, feeds with an initial boiling point and/or a T5 boiling point and/or T10 boiling point of at least 600° F. (~316° C.), or at least 650° F. (~343° C.), or at least 700° F. (371° C.), or at least 750° F. (~399° C.). Additionally or alternatively, the final boiling point and/or T95 boiling point and/or T90 boiling point of the feed can be 1100° F. (~593° C.) or less, or 1050° F. (~566° C.) or less, or 1000° F. (~538° C.) or less, or 950° F. (~510° C.) or less. In particular, a feed can have a T5 to T95 boiling range of 600° F. (~316° C.) to 1100° F. (~593° C.), or a T5 to T95 boiling range of 650° F. (~343° C.) to 1050° F. (~566° C.), or a T10 to T90 boiling range of 650° F. (~343° C.) to 1050° F. (~566° C.) Optionally, if the hydroprocessing is also used to form fuels, it can be possible to use a feed that includes a lower boiling range portion. Such a feed can have an initial boiling point and/or a T5 boiling point and/or T10 boiling point of at least 350° F. (~177° C.), or at least 400° F. (~204° C.), or at least 450° F. (~232° C.). In particular, such a feed can have a T5 to T95 boiling range of 350° F. (~177° C.) to 1100° F. (~593° C.), or a T5 to T95 boiling range of 450° F. (~232° C.) to 1050° F. (~566° C.), or a T10 to T90 boiling range of 350° F. (~177° C.) to 1050° F. (~566° C.).

In some aspects, the raffinate feed for forming the bright stock can correspond to a "sweet" feed, so that the sulfur content of the feed is 0 wppm to 300 wppm, or 1 wppm to 300 wppm and/or the nitrogen content is 0 wppm to 100 wppm, or 1 wppm to 100 wppm. In other aspects, the feed for forming the bright stock can correspond to a feed that has not been hydroprocessed and/or that has not been hydroprocessed sufficiently to form a "sweet" feed. In such aspects, the feed for bright stock production can have a sulfur content of 0 wppm to 20000 wppm, or 300 wppm to 20000 wppm. Additionally or alternately, in such aspects, the rafffinate feed for bright stock production can have a nitrogen content of 0 wppm to 10000 wppm, or 100 wppm to 10000 wppm.

In some embodiments, at least a portion of the feed can correspond to a feed derived from a biocomponent source. In this discussion, a biocomponent feedstock refers to a hydrocarbon feedstock derived from a biological raw material component, from biocomponent sources such as vegetable, animal, fish, and/or algae. Note that, for the purposes of this document, vegetable fats/oils refer generally to any plant based material, and can include fat/oils derived from a source such as plants of the genus Jatropha. Generally, the biocomponent sources can include vegetable fats/oils, animal fats/oils, fish oils, pyrolysis oils, and algae lipids/oils, as well as components of such materials, and in some embodiments can specifically include one or more type of lipid compounds. Lipid compounds are typically biological compounds that are insoluble in water, but soluble in nonpolar (or fat) solvents. Non-limiting examples of such solvents include alcohols, ethers, chloroform, alkyl acetates, benzene, and combinations thereof.

Characterization of Bright Stock Feed and Product Samples with FTICR

Briefly, FTICR is a particular type of mass spectrometry that allows for detailed resolution of the composition of a sample. Unlike many types of mass spectrometry, an ion cyclotron resonance mass spectrometer does not detect species based on collisions with a detector. Instead, after forming ions from the species in a sample, the ions are trapped within the magnetic field, resulting in a cyclotron as the ions traverse an (approximately) circular path within the magnetic field. The speed of each ion varies depending on the mass at a given energy. This speed differences allows the electric field generated by different ions traveling in the magnetic field to be detected and distinguished. This time-domain electric signal is converted by Fourier transform into frequency-domain signals that correspond to the different types of ions in the magnetic field. This allows for detailed differentiation between the compounds within a sample.

Figure 2:
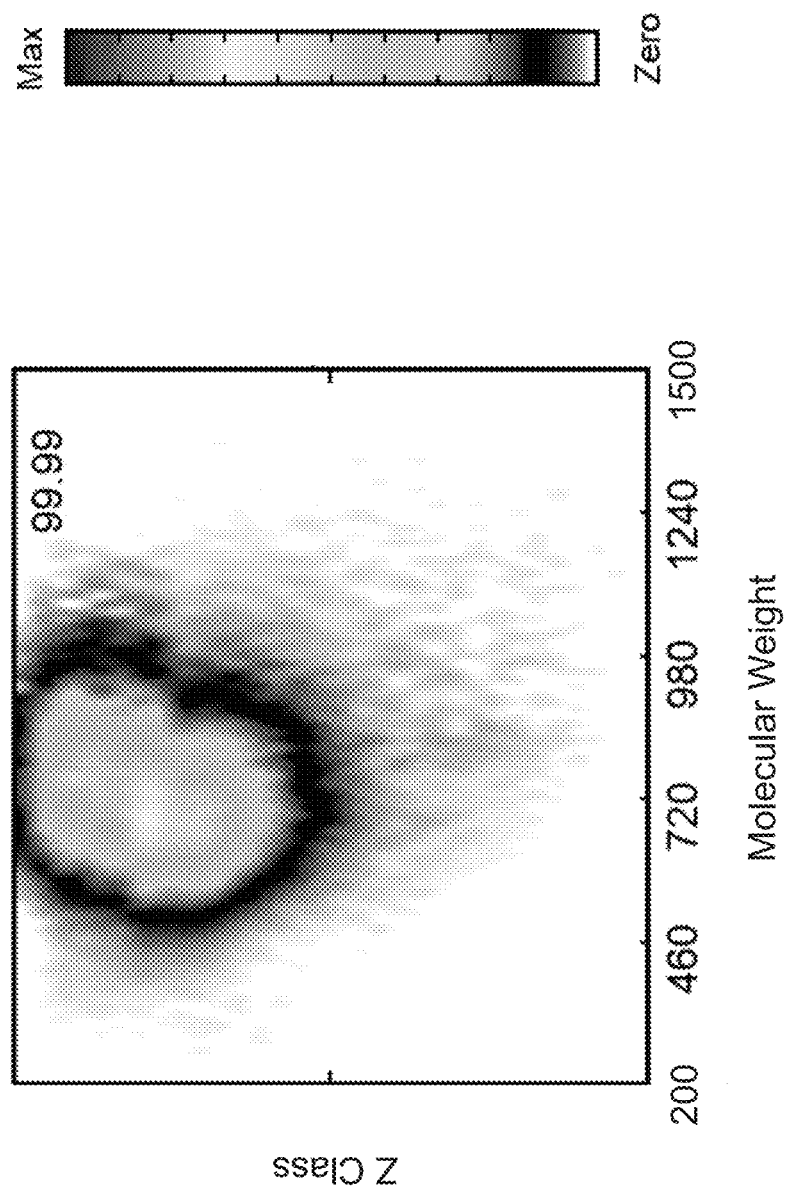
FIG. 2 shows an FTICR characterization of the composition of a dewaxed oil produced by solvent dewaxing of the feed for bright stock production in FIG. 1.
Figure 3:
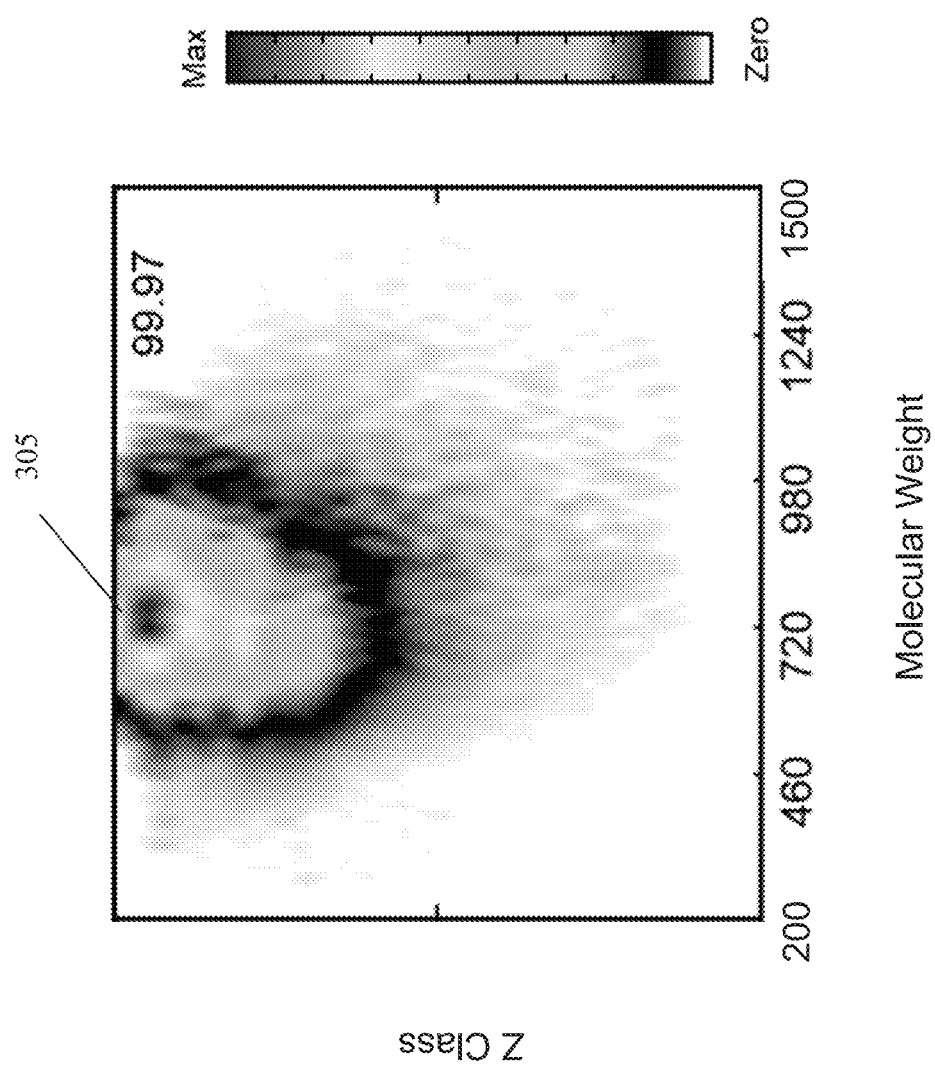
FIG. 3 shows FTICR characterizations of the composition of a wax fraction produced by solvent dewaxing of the feed for bright stock production in FIG. 1.

FIGS. 1 to 3 show examples of the types of compositional details that can be identified using FTICR mass spectrometry. FIG. 1 shows output data from performing FTICR on a raffinate feedstock for bright stock production. FIG. 2 shows similar output data for a dewaxed oil product generated by solvent dewaxing of the feed in FIG. 1. FIG. 3 corresponds to output data for a wax fraction produced by the same solvent dewaxing process. In each of FIG. 1, FIG. 2, and FIG. 3, the vertical axis corresponds to the Z-class of the compounds, while the horizontal axis represents the molecular weight of the compounds. As shown by the legend in each figure, the intensity of the FTICR signal is also provided, indicating the amount of the particular combination of Z-class and molecular weight. For FIGS. 1-3, the same relative scale is used for intensity.

The FTICR plots in FIGS. 1-3 demonstrate the ability of FTICR to provide compositional information about a feedstock and/or resulting product fractions. FIG. 1 shows the distribution of compounds in the raffinate feedstock based on Z-class and molecular weight. As shown in FIG. 1, the raffinate feedstock has a broad distribution of compounds. Roughly 95 wt % of the compounds have a Z-class of 2 to −29 with a molecular weight between roughly 500 g/mol and 1000 g/mol. As further shown in FIG. 1, the majority of the compounds have a Z-class of roughly −2 to −20, with a molecular weight of roughly 600 g/mol to 900 g/mol.

The dewaxed oil product in FIG. 2 has a distribution of compounds that is somewhat similar to FIG. 1. Roughly 95 wt % of the compounds have a Z-class of 2 to −29 with a molecular weight between roughly 500 g/mol and 1000 g/mol, and the majority of the compounds also have a Z-class of roughly −2 to −20 with a molecular weight of roughly 600 g/mol to 900 g/mol. There may also be a modest shift toward lower molecular weight compounds.

The compositional profile in FIG. 3 differs from the compositional profiles in FIG. 1 and FIG. 2 in several ways. First, a description of the profile based on boundaries corresponding to 95 wt % of the compounds corresponds to a Z-class of 2 to −25 and a molecular weight of roughly 550 to 1000. Additionally, the compositional profile for the wax in FIG. 3 has a distinct maximum for compounds with a Z-class of 0 to 6 and a molecular weight roughly 720 g/mol to 800 g/mol. This maximum in the profile corresponds to the darker area labeled as feature 305 in FIG. 3.

FTICR can also be used to compare the nature of a bright stock composition with a typical heavy neutral composition. It has been discovered that the chemical composition of the wax in bright stock is qualitatively different from the wax in a heavy neutral sample. These qualitative differences can result in different behavior for the wax in a bright stock sample. By using FTICR to understand these qualitative differences, dewaxing conditions for producing a bright stock sample can be selected to achieve one or more desired properties.

Figure 4:
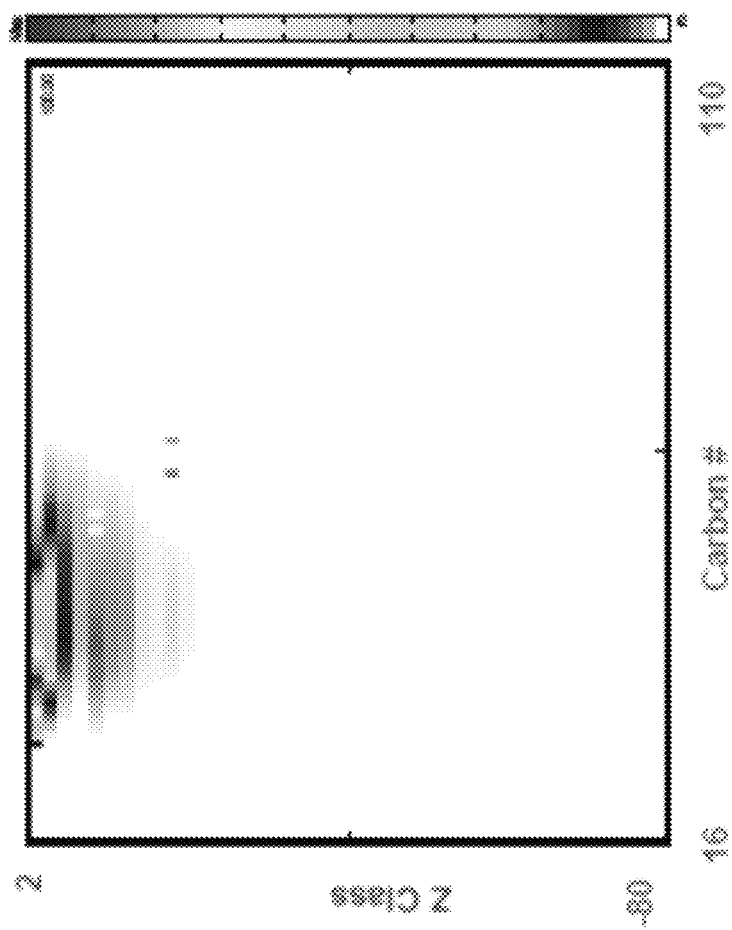
FIG. 4 shows FTICR characterization of the wax fraction generated during solvent dewaxing to form a heavy neutral base stock.

FIG. 4 shows FTICR data for wax generated by solvent dewaxing of a feed for forming a heavy neutral base stock. In FIG. 4, the wax from performing solvent dewaxing to make a heavy neutral base stock is characterized based on Z-class versus carbon number, as opposed to molecular weight. However, the qualitative differences between the wax from a heavy neutral feed and a bright stock feed are still readily illustrated. In FIG. 3, the FTICR compositional profile shows that a substantial portion of the dry wax removed from bright stock has a Z-class of less than −20 and/or a molecular weight greater than 700 g/mol. By contrast, dry wax formed from dewaxing a feedstock for making a heavy neutral product has a more limited compositional profile, with few compounds having a Z-class of less than −10. The dry wax in FIG. 4 also has relatively few compounds with a carbon number greater than 50, which roughly corresponds to having few compounds with a molecular weight greater than 700 g/mol. Based on the differences in the nature of the wax removed from a bright stock feed versus a heavy neutral feed when forming a base stock, the dewaxing conditions can be adjusted improve the dewaxing step for forming a bright stock.

Figure 5:
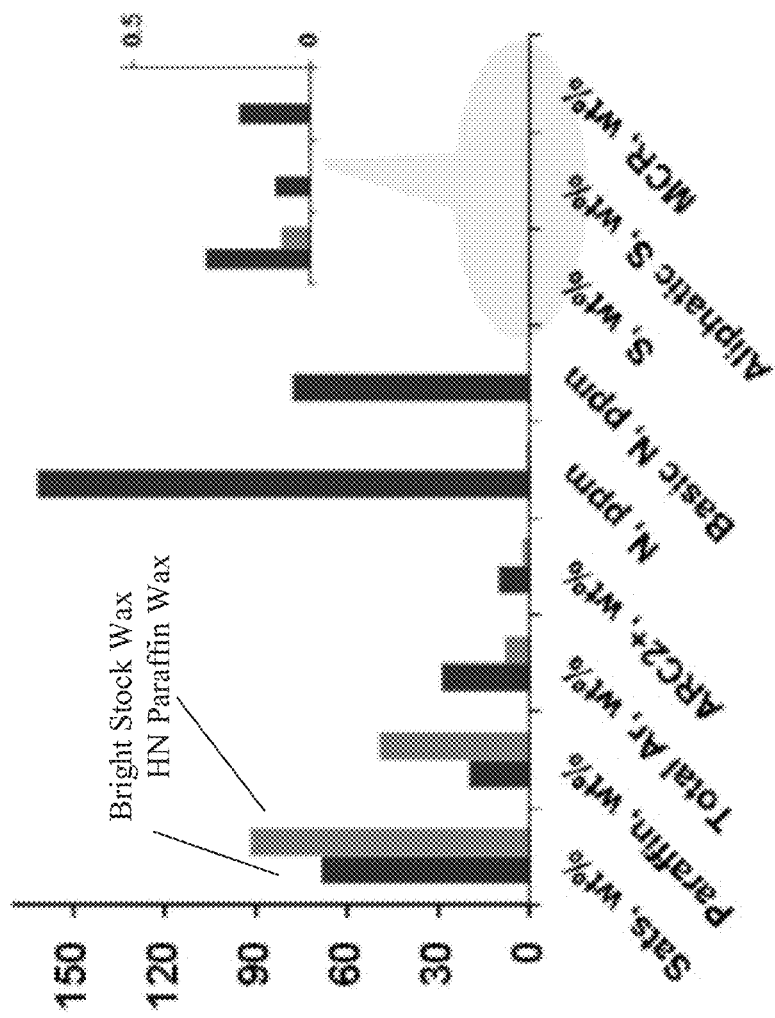
FIG. 5 shows a comparison of bulk properties for a wax fraction produced during bright stock production and a wax fraction produced during heavy neutral base stock production.
Figure 6:
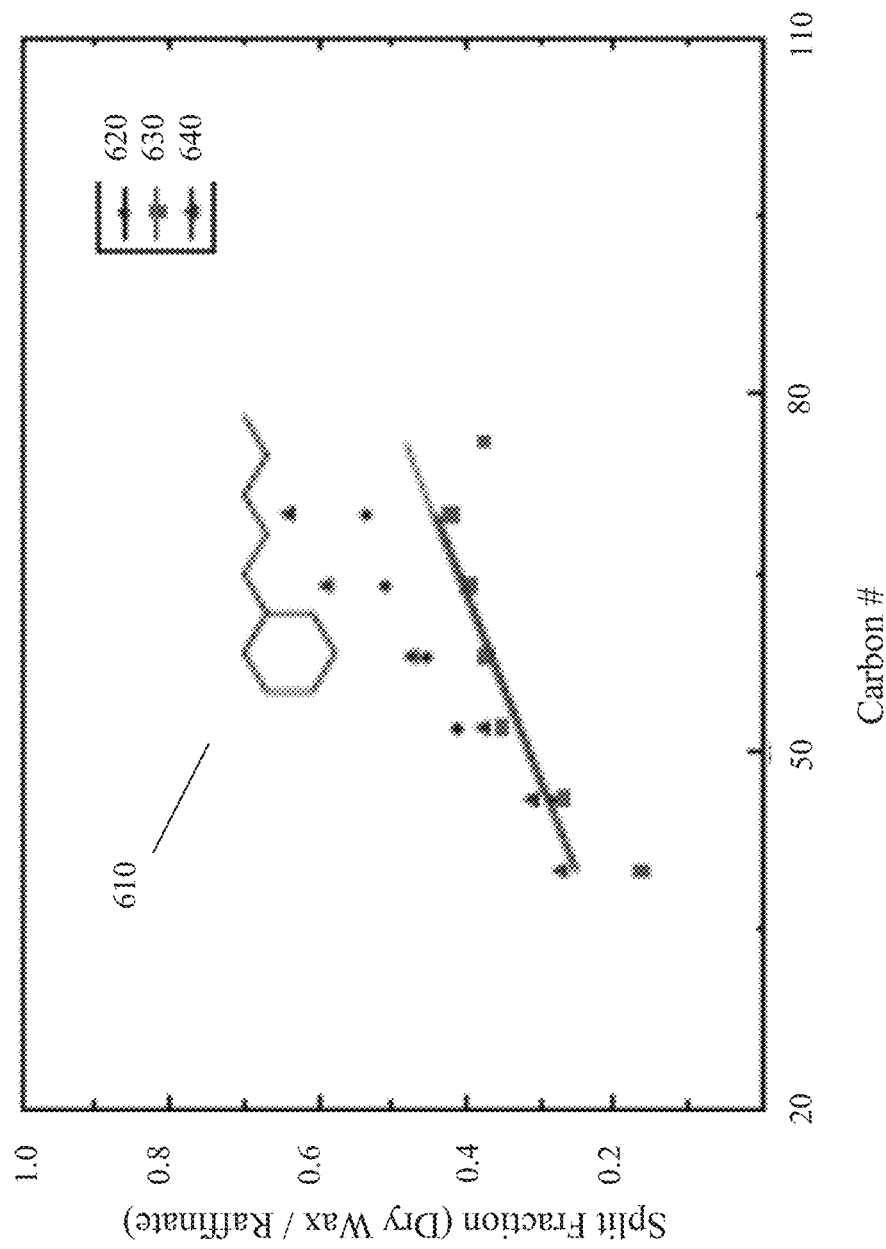
FIG. 6 shows FTICR characterization of how a homologous series of compounds in a solvent dewaxing feedstock for bright stock formation is split between dewaxed oil and wax.

The differences between the dry wax from a bright stock production process and a heavy neutral production process are further illustrated in FIG. 5, which shows various bulk properties for the dry waxes from FIGS. 3 and 4. The bulk properties for the bright stock dry wax and heavy neutral dry wax in FIG. 5 include wt % saturates, wt % paraffins, wt % aromatics, wt % 2+ ring aromatics, nitrogen and basic nitrogen content (in wppm) sulfur and aliphatic sulfur content (in wt %), and micro carbon residue (wt %). As shown in FIG. 5, bright stock dry wax has a lower paraffin and saturates content than a corresponding heavy neutral wax, while having higher aromatics content, including higher 2+ ring aromatic content. It is noted that the paraffin content in FIG. 5 for the bright stock wax is between 10 wt % and 15 wt %, while the aromatics content is between 20 wt % and 30 wt %. This is in contrast to the heavy neutral wax, which has nearly 50 wt % paraffin content while having a total aromatics content of less than 10 wt %. Additionally, the bright stock wax has appreciable contents of nitrogen, basic nitrogen, aliphatic sulfur, and micro carbon residue. By contrast, the heavy neutral wax has sufficiently low content of these components that the heavy neutral can be characterized as having substantially no content of these components.

Based on the compositional characteristics of brighstock feed and products, as illustrated by FTICR and bulk properties, the conditions for a bright stock production process can be modified in various manners. For example, the FTICR information related to one or more Z-classes within a bright stock sample, optionally in combination with molecular weight information, can be used to determine the amount of dewaxing severity that is needed to achieve a desired pour point for the resulting bright stock product. One option can be to determine a correlation (such as a correlation derived over a plurality of feed and product samples) where reducing the wt % of one or more Z-class/molecular weight combinations below a threshold wt % results in a desired pour point for the bright stock product. Once this correlation is developed, the FTICR compositional information for a particular feed sample can be used to determine the amount of material that needs to be removed to achieve the one or more threshold values. The severity of the dewaxing step (either solvent or catalytic) can then be selected to generate a product fraction that substantially meets the threshold values for the selected Z-class/molecular weight combinations.

As another example, a goal of a solvent dewaxing process could be to improve the processing conditions so that the process can operate in an efficient manner. This could include, for example, selecting solvent dewaxing conditions that result in a desired thickness for the filter cake of wax that is removed from the feed during the solvent dewaxing. By using FTICR to characterize the feed, the amount of wax and/or the nature of the wax that will be removed during solvent dewaxing can be determined. Based on the amount of wax removed, the solvent dewaxing conditions can be modified, such as by selecting a feed rate to the solvent dewaxing process so that the wax removed from the feed results in a desired filter cake size under the processing conditions.

Figure 10:
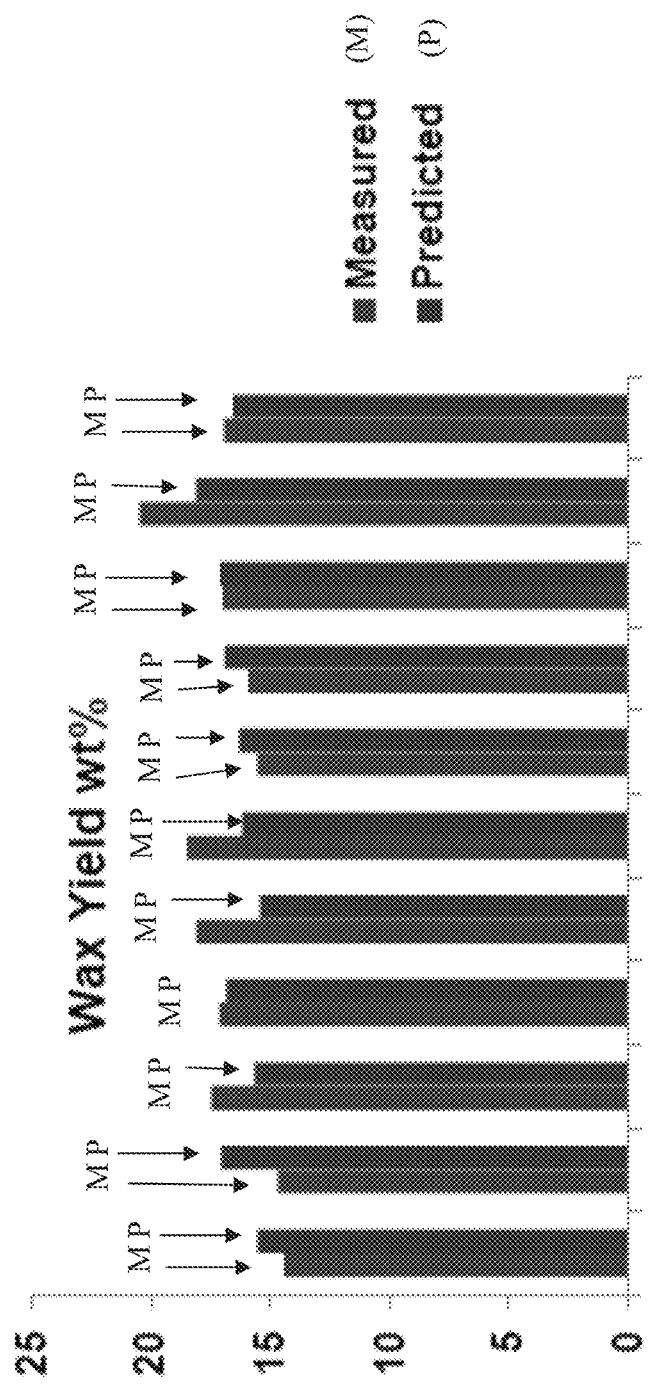
FIG. 10 shows a comparison of measured wax yields from solvent dewaxing and predicted wax yields based on FTICR compositional characterization of the raffinate feed to solvent dewaxing and the corresponding dewaxing conditions.

FIG. 10 shows an example where FTICR compositional information was used to determine a wax yield for a solvent dewaxing process based on the solvent dewaxing conditions and the compositional components of various bright stock feeds. A correlation was developed based on the amounts of one or more Z-class/molecular weight combinations within various bright stocks, in combination with various solvent dewaxing conditions. Based on an initial data set, a model was developed for predicting wax yield based on the nature of a feed (as determined by FTICR) and the solvent dewaxing conditions. FIG. 10 shows the wax yield predictions for solvent dewaxing of feeds from eleven different crude sources, along with the actual measured yields. For each pair of bars, the measured yield corresponds to the left bar, while the predicted yield corresponds to the right bar. As shown in FIG. 10, the FTICR data allowed for construction of a model that provided reasonably accurate results for wax yield. Based on this type of model, for a given feed sample, FTICR characterization can be used to select conditions to achieve a desired wax yield. The desired wax yield, for example, could be selected so that the amount of residual wax remaining in the bright stock corresponds to less than a threshold value. The threshold for residual wax could be based on a correlation of residual wax content and one or more cold flow property values. Additionally or alternatively, the desired wax yield could be based on removing a target percentage of wax from the feed when producing the bright stock product. Still other types of correlations could also be used to allow the residual wax content, and/or any other property determined in part by FTICR, to be used to select dewaxing conditions in order to achieve a desired property for the resulting bright stock product(s).

It is noted that the bulk properties of the feedstock for forming a bright stock can also be used as a factor. For example, hydrotreating and/or hydrocracking a feedstock can result in both sulfur removal and aromatic saturation of the feedstock. The sulfur content and aromatics content of a feed are characterizations that can be routinely performed in many refinery settings. For a hydrotreated (and or hydrocracked) feedstock, the sulfur and/or aromatics content of the hydrotreated feedstock may change over time as the hydrotreating (and/or hydrocracking) catalyst ages. This can result in changes in the composition of the wax components in the hydrotreated (and/or hydrocracked) feedstock. The sulfur content, aromatics content, or a combination thereof can be used in conjunction with the FTICR characterization to provide further refinements for a dewaxing process, so that the dewaxing process can continue to meet desired targets for the resulting base stock product even though the input feedstock is being changed.

Figure 7:
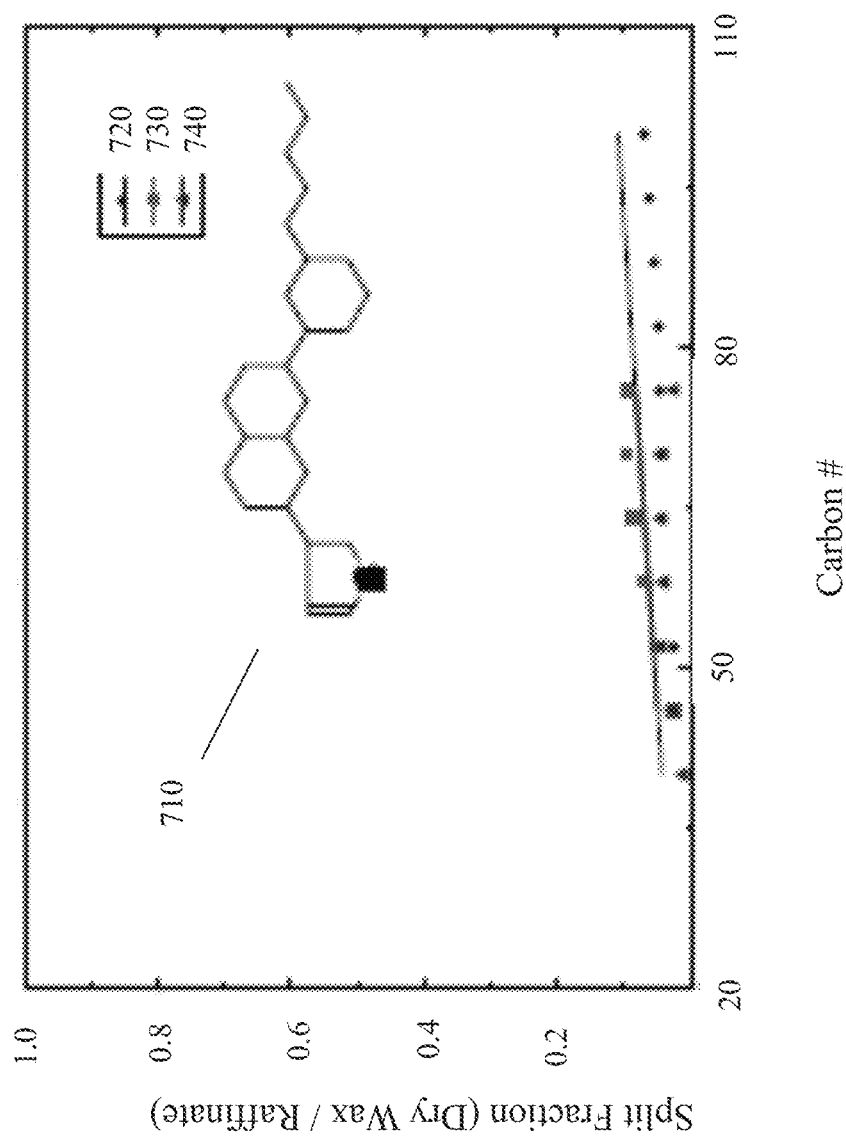
FIG. 7 shows another example of FTICR characterization of how a homologous series of compounds in a solvent dewaxing feedstock for bright stock formation is split between dewaxed oil and wax.
Figure 8:
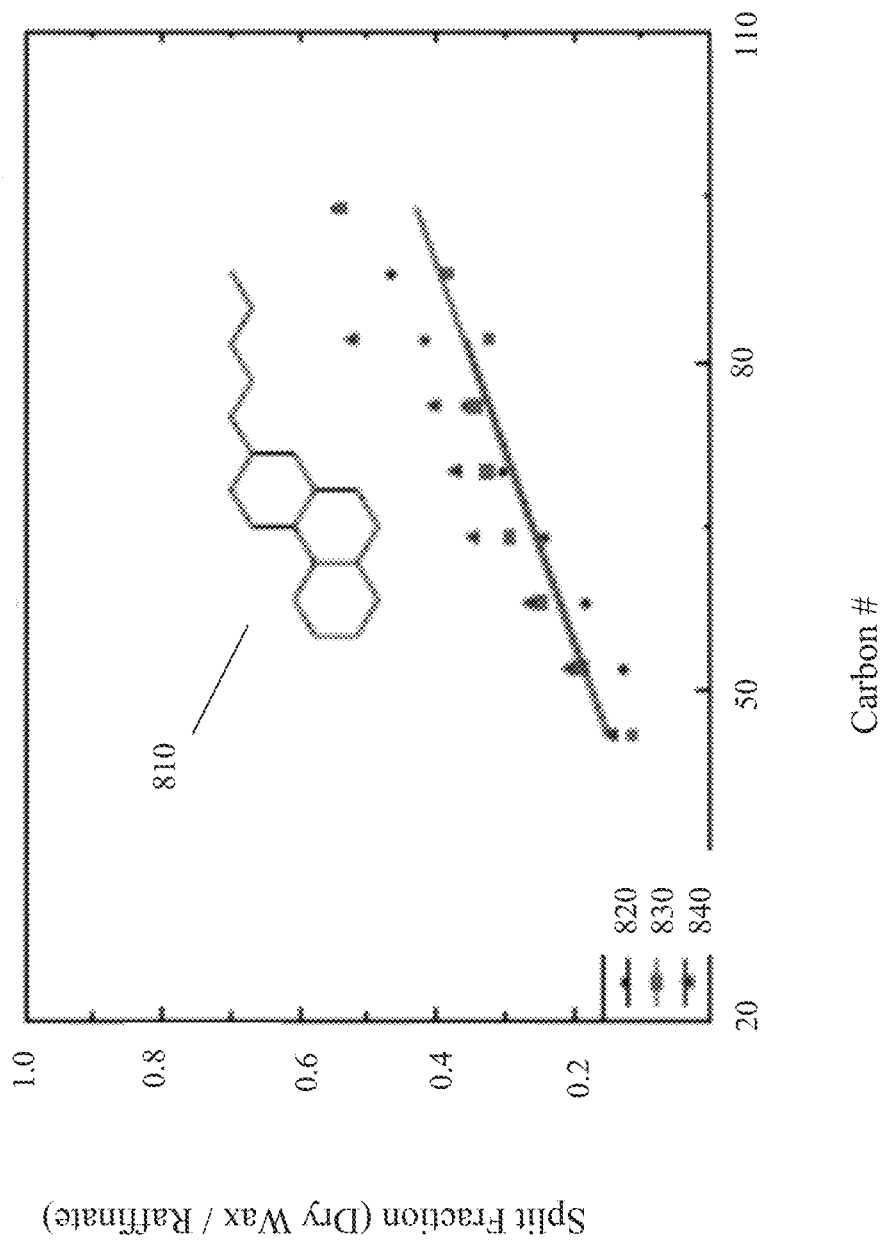
FIG. 8 shows another example of FTICR characterization of how a homologous series of compounds in a solvent dewaxing feedstock for bright stock formation is split between dewaxed oil and wax.
Figure 9:
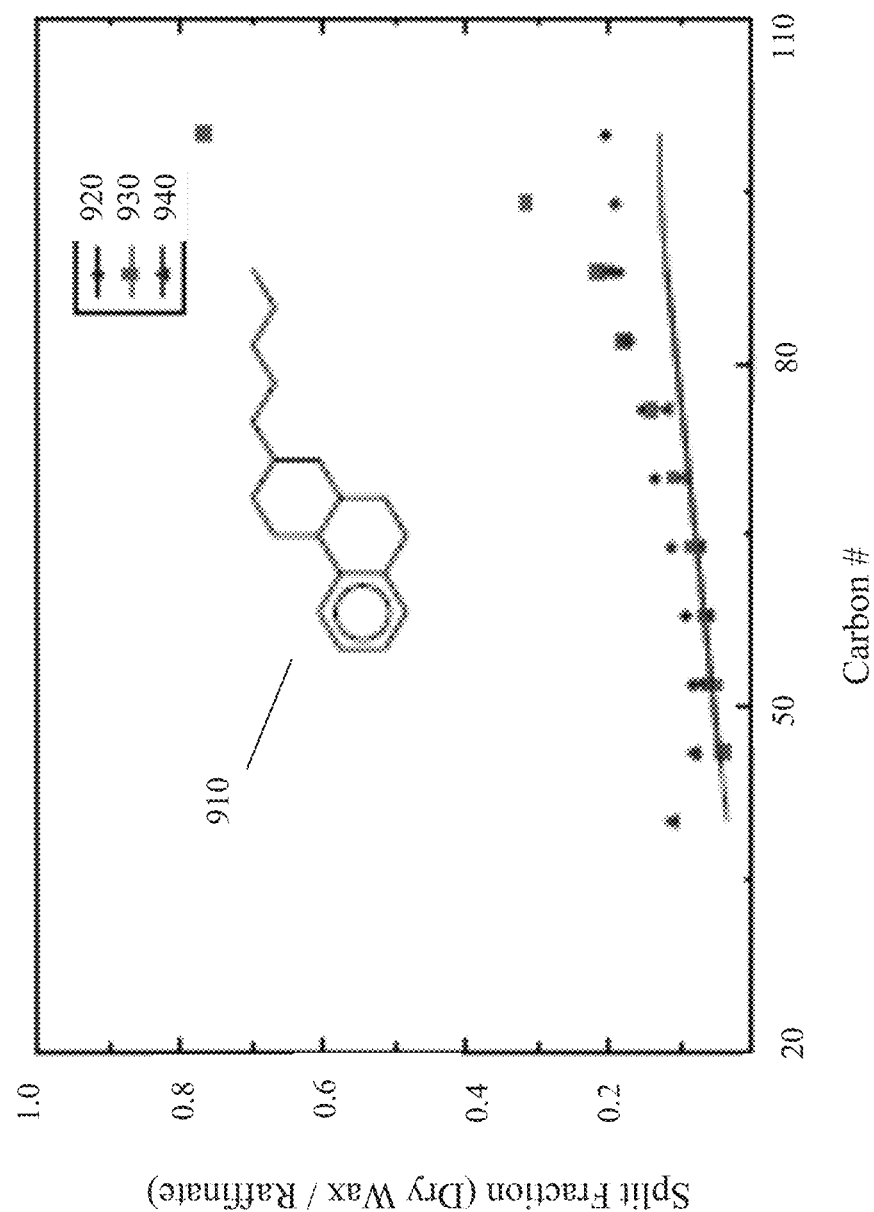
FIG. 9 shows another example of FTICR characterization of how a homologous series of compounds in a solvent dewaxing feedstock for bright stock formation is split between dewaxed oil and wax.

Still another type of data analysis that can be performed using FTICR is shown in FIGS. 6-9. In FIGS. 6-9, FTICR data for four different series of homologous compounds within three different raffinate feeds are illustrated. The data in FIGS. 6-9 show the weight percentage of a given member of the homologous compounds that becomes part of the wax product after solvent dewaxing. As shown in FIGS. 6-9, within a homologous series, the weight percent of a given homolog that becomes part of the wax product tends to increase with increasing carbon number. For example, in FIG. 6, the type of compound corresponding to the series of homologs is shown 610. Data series 620, 630, and 640 show the amount of each member in the series that becomes part of the wax product for three different types of raffinate feeds. Similarly, FIG. 7 shows data series 720, 730, and 740 for another series of homologs represented by compound 710; FIG. 8 shows data series 820, 830, and 840 for another series of homologs represented by compound 810; and FIG. 9 shows data series 920, 930, and 940 for another series of homologs represented by compounds 910.

Based on the type of homologous series data shown in FIG. 6, FIG. 7, FIG. 8, and FIG. 9, one or more homologous series of compounds can be characterized in the feed and/or products in order to determine the dewaxing severity for achieving a desired property, such as a target pour point, target cloud point, target cold filter plugging point, or another cold flow property. The dewaxing severity can be modified, for example, by modifying the dewaxing solvent, such as the ratio of components in a solvent including two or more solvent components, modifying the target feed rate, and/or modifying the target wax cake size. This type of characterization of homologous series data can be done in place of and/or in addition to using Z-class and molecular weight to characterize wax components within a feed or product.

It is noted that the data shown in FIGS. 1-10 corresponds to data for using solvent dewaxing to produce a bright stock product. Solvent dewaxing results in a both a bright stock fraction and a wax fraction, so that the properties of two different products are potentially available (in addition to the feedstock) for developing any model correlations that can be useful for predicting properties based on FTICR characterization. For catalytic dewaxing, typically only a single liquid effluent is generated. However, the types of information that can be characterized for the liquid effluent from a catalytic bright stock production process can otherwise be similar to the types of compositional information described above for a solvent dewaxing process.

Solvent Dewaxing

Solvent dewaxing typically involves mixing a feed with chilled dewaxing solvent to form an oil-solvent solution. Precipitated wax is thereafter separated by, for example, filtration. The temperature and solvent are selected so that the oil is dissolved by the chilled solvent while the wax is precipitated.

An example of a suitable solvent dewaxing process involves the use of a cooling tower where solvent is prechilled and added incrementally at several points along the height of the cooling tower. The oil-solvent mixture is agitated during the chilling step to permit substantially instantaneous mixing of the prechilled solvent with the oil. The prechilled solvent is added incrementally along the length of the cooling tower so as to maintain an average chilling rate at or below 10° F. (~6° C.) per minute, usually between about 1 to about 5° F. (~0.6° C.-3° C.) per minute. The final temperature of the oil-solvent/precipitated wax mixture in the cooling tower will usually be between 0 and 50° F. (−17.8 to 10° C.). The mixture may then be sent to a scraped surface chiller to separate precipitated wax from the mixture. The accumulated wax on the surface chiller can be referred to as a filter cake. In some aspects, FTICR data can be used to characterize the feed for bright stock production, so that solvent dewaxing conditions can be selected to achieve a desired thickness for this filter cake.

An example of a scraped surface chiller can be a rotary drum vacuum filter. Such a filter can include a horizontal, cylindrical drum, the lower portion of which is immersed in a trough containing the wax slurry, a filter medium or cloth covering the horizontal surface of the drum, means for applying both vacuum and pressure thereto and means for washing and removing wax cake deposited on the cloth as the drum continuously rotates around its horizontal axis. In these filters the drum is divided into compartments or sections, each section being connected to a rotary (trunnion) valve and then to a discharge head. The wax slurry is fed into the filter trough and as the drum rotates, the faces of the sections pass successively through the slurry. In a vacuum drum filter, a vacuum is applied to the sections as they pass through the slurry, thereby drawing oily filtrate through the filter medium and depositing wax therein in the form of a cake. As the cake leaves the slurry it contains only filtrate which is removed therefrom by the continued application of vacuum, along with wash solvent which is evenly distributed or sprayed on the surface of the cake, thereby forming a solvent-rich wash filtrate. Finally, the washed wax cake is removed by a scraper which is assisted by means of blow gas applied to each section of the drum as it rotates and reaches the scraper. By making appropriate adjustments to the trunnion valve, the wash filtrate may be collected separately from the oily filtrate.

Typically, filtration temperatures for the waxy slurries range from −30° F. to +25° F. (~−35° C. to −4° C.) for ketone solvents and from −45° F. to −25° F. (~−42° C. to −30° C.) for autorefrigerant solvents such as propane and propylene/acetone. The wash solvent can typically be at or slightly below the filtration temperature.

Representative dewaxing solvents are aliphatic ketones having 3-6 carbon atoms such as methyl ethyl ketone and methyl isobutyl ketone, low molecular weight hydrocarbons such as propane and butane, and mixtures thereof. The solvents may be mixed with other solvents such as benzene, toluene or xylene.

In general, the amount of solvent added will be sufficient to provide a liquid/solid weight ratio between the range of 5/1 and 20/1 at the dewaxing temperature and a solvent/oil volume ratio between 1.5/1 to 5/1. The solvent dewaxed oil can be dewaxed to a pour point of −6° C. or less, or −10° C. or less, or −15° C. or less, depending on the nature of the target lubricant base stock product. Additionally or alternately, the solvent dewaxed oil can be dewaxed to a cloud point of −2° C. or less, or −5° C. or less, or −10° C. or less, depending on the nature of the target lubricant base stock product. The resulting solvent dewaxed oil can be suitable for use in forming one or more types of Group I base stocks. Preferably, a bright stock formed from the solvent dewaxed oil can have a cloud point below −5° C. The resulting solvent dewaxed oil can have a viscosity index of at least 90, or at least 95, or at least 100. Preferably, at least 10 wt % of the resulting solvent dewaxed oil (or at least 20 wt %, or at least 30 wt %) can correspond to a Group I bright stock having a kinematic viscosity at 100° C. of 20 cSt or more, or 24 cSt or more, or 30 cSt or more, such as up to 120 cSt or possibly still higher.

After performing one or more initial filtrations to form dewaxed oil and wax, the wax can be de-oiled to improve the quality of the wax and/or further recover a dewaxed oil product. The de-oiling process can be performed using a similar type of methodology, where solvent is added to the wax product followed by separation of oil from wax using a scraped surface chiller. It is believed that the benefits of operating with as solvent beyond the miscibility point can also be realized during de-oiling. However, the dewaxed oil removed from the wax cake during a de-oiling process can tend to be of a lower kinematic viscosity, such as a having a kinematic viscosity at 100° C. of 14 cSt to 30 cSt.

Catalytic Dewaxing

For catalytic dewaxing, suitable dewaxing catalysts can include molecular sieves such as crystalline aluminosilicates (zeolites). In an embodiment, the molecular sieve can comprise, consist essentially of, or be ZSM-22, ZSM-23, ZSM-48. Optionally but preferably, molecular sieves that are selective for dewaxing by isomerization as opposed to cracking can be used, such as ZSM-48, ZSM-23, or a combination thereof. Additionally or alternately, the molecular sieve can comprise, consist essentially of, or be a 10-member ring 1-D molecular sieve, such as EU-2, EU-11, ZBM-30, ZSM-48, or ZSM-23. ZSM-48 is most preferred. Note that a zeolite having the ZSM-23 structure with a silica to alumina ratio of from about 20:1 to about 40:1 can sometimes be referred to as SSZ-32. Optionally but preferably, the dewaxing catalyst can include a binder for the molecular sieve, such as alumina, titania, silica, silica-alumina, zirconia, or a combination thereof, for example alumina and/or titania or silica and/or zirconia and/or titania.

In some aspects, the dewaxing catalysts used in processes according to the invention are catalysts with a low ratio of silica to alumina. For example, for ZSM-48, the ratio of silica to alumina in the zeolite can be about 100:1 or less, such as about 90:1 or less, or about 75:1 or less, or about 70:1 or less. Additionally or alternately, the ratio of silica to alumina in the ZSM-48 can be at least about 50:1, such as at least about 60:1, or at least about 65:1.

In various aspects, the catalysts according can further include a metal hydrogenation component. The metal hydrogenation component is typically a Group VI and/or a Group VIII metal. Preferably, the metal hydrogenation component can be a combination of a non-noble Group VIII metal with a Group VI metal. Suitable combinations can include Ni, Co, or Fe with Mo or W, preferably Ni with Mo or W.

The metal hydrogenation component may be added to the catalyst in any convenient manner. One technique for adding the metal hydrogenation component is by incipient wetness. For example, after combining a zeolite and a binder, the combined zeolite and binder can be extruded into catalyst particles. These catalyst particles can then be exposed to a solution containing a suitable metal precursor. Alternatively, metal can be added to the catalyst by ion exchange, where a metal precursor is added to a mixture of zeolite (or zeolite and binder) prior to extrusion.

The amount of metal in the catalyst can be at least 0.1 wt % based on catalyst, or at least 0.5 wt %, or at least 1.0 wt %, or at least 2.5 wt %, or at least 5.0 wt %, based on catalyst. The amount of metal in the catalyst can be 20 wt % or less based on catalyst, or 10 wt % or less, or 5 wt % or less, or 2.5 wt % or less, or 1 wt % or less. For embodiments where the metal is a combination of a non-noble Group VIII metal with a Group VI metal, the combined amount of metal can be from 0.5 wt % to 20 wt %, or 1 wt % to 15 wt %, or 2.5 wt % to 10 wt %.

The dewaxing catalysts useful in processes according to the invention can also include a binder. In some embodiments, the dewaxing catalysts used in process according to the invention are formulated using a low surface area binder, a low surface area binder represents a binder with a surface area of 100 m$^2$/g or less, or 80 m$^2$/g or less, or 70 m$^2$/g or less. Additionally or alternately, the binder can have a surface area of at least about 25 m$^2$/g. The amount of zeolite in a catalyst formulated using a binder can be from about 30 wt % zeolite to 90 wt % zeolite relative to the combined weight of binder and zeolite. Preferably, the amount of zeolite is at least about 50 wt % of the combined weight of zeolite and binder, such as at least about 60 wt % or from about 65 wt % to about 80 wt %.

Without being bound by any particular theory, it is believed that use of a low surface area binder reduces the amount of binder surface area available for the hydrogenation metals supported on the catalyst. This leads to an increase in the amount of hydrogenation metals that are supported within the pores of the molecular sieve in the catalyst.

A zeolite can be combined with binder in any convenient manner. For example, a bound catalyst can be produced by starting with powders of both the zeolite and binder, combining and mulling the powders with added water to form a mixture, and then extruding the mixture to produce a bound catalyst of a desired size. Extrusion aids can also be used to modify the extrusion flow properties of the zeolite and binder mixture. The amount of framework alumina in the catalyst may range from 0.1 to 3.33 wt %, or 0.1 to 2.7 wt %, or 0.2 to 2 wt %, or 0.3 to 1 wt %.

Effective conditions for catalytic dewaxing of a feedstock in the presence of a dewaxing catalyst can include a temperature of from 280° C. to 450° C., preferably 343° C. to 435° C., a hydrogen partial pressure of from 3.5 MPag to 34.6 MPag (500 psig to 5000 psig), preferably 4.8 MPag to 20.8 MPag, and a hydrogen circulation rate of from 178 m$^3$/m$^3$ (1000 SCF/B) to 1781 m$^3$/m$^3$ (10,000 scf/B), preferably 213 m$^3$/m$^3$ (1200 SCF/B) to 1068 m$^3$/m$^3$ (6000 SCF/B). The LHSV can be from about 0.2 h$^{-1}$ to about 10 h$^{-1}$, such as from about 0.5 h$^{-1}$ to about 5 h$^{-1}$ and/or from about 1 h$^{-1}$ to about 4 h$^{-1}$.

Additional Hydroprocessing—Hydrotreating, Hydrocracking, and Hydrofinishing

In addition to catalytic dewaxing, lubricant base oils are often exposed to hydroprocessing conditions (in the presence of corresponding suitable catalysts) corresponding to hydrotreating, hydrocracking, and/or aromatic saturation conditions. The order of the catalytic dewaxing and other hydroprocessing steps can vary. In various aspects, at least some hydrotreating and/or hydrocracking may be performed prior to dewaxing to reduce sulfur content to desired levels and/or to modify the viscosity index of the resulting lubricant base stock.

The reaction conditions during hydrotreatment and/or hydrocracking can be selected to generate a desired level of conversion of a feed. Any convenient type of reactor, such as fixed bed (for example trickle bed) reactors can be used. Conversion of the feed can be defined in terms of conversion of molecules that boil above a temperature threshold to molecules below that threshold. The conversion temperature can be any convenient temperature, such as ~700° F. (370° C.) or 1050° F. (566° C.). The amount of conversion can correspond to the total conversion of molecules within the combined hydrotreatment and hydrocracking stages for the feed. Suitable amounts of conversion of molecules boiling above 1050° F. (566° C.) to molecules boiling below 566° C. include 30 wt % to 90 wt % conversion relative to 566° C., or 30 wt % to 80 wt %, or 30 wt % to 70 wt %, or 40 wt % to 90 wt %, or 40 wt % to 80 wt %, or 40 wt % to 70 wt %, or 50 wt % to 90 wt %, or 50 wt % to 80 wt %, or 50 wt % to 70 wt %. In particular, the amount of conversion relative to 566° C. can be 30 wt % to 90 wt %, or 30 wt % to 70 wt %, or 50 wt % to 90 wt %. Additionally or alternately, suitable amounts of conversion of molecules boiling above ~700° F. (370° C.) to molecules boiling below 370° C. include 10 wt % to 70 wt % conversion relative to 370° C., or 10 wt % to 60 wt %, or 10 wt % to 50 wt %, or 20 wt % to 70 wt %, or 20 wt % to 60 wt %, or 20 wt % to 50 wt %, or 30 wt % to 70 wt %, or 30 wt % to 60 wt %, or 30 wt % to 50 wt %. In particular, the amount of conversion relative to 370° C. can be 10 wt % to 70 wt %, or 20 wt % to 50 wt %, or 30 wt % to 60 wt %.

The hydroprocessed effluent can also be characterized based on the product quality. In aspects where catalytic dewaxing is performed, after hydroprocessing (hydrotreating and/or hydrocracking), the 370° C.+ portion of the hydroprocessed effluent can have a sulfur content of 500 wppm or less, or 200 wppm or less, or 50 wppm or less (such as down to ~0 wppm). Additionally or alternately, the 370° C.+ portion of the hydroprocessed effluent can have a nitrogen content of 200 wppm or less, or 100 wppm or less, or 50 wppm or less (such as down to ~0 wppm).

In various aspects, the feed can be exposed to a hydrotreating catalyst under effective hydrotreating conditions. The catalysts used can include conventional hydroprocessing catalysts, such as those comprising at least one Group VIII non-noble metal (Columns 8-10 of IUPAC periodic table), preferably Fe, Co, and/or Ni, such as Co and/or Ni; and at least one Group VI metal (Column 6 of IUPAC periodic table), preferably Mo and/or W. Such hydroprocessing catalysts optionally include transition metal sulfides that are impregnated or dispersed on a refractory support or carrier such as alumina and/or silica. The support or carrier itself typically has no significant/measurable catalytic activity. Substantially carrier- or support-free catalysts, commonly referred to as bulk catalysts, generally have higher volumetric activities than their supported counterparts.

The catalysts can either be in bulk form or in supported form. In addition to alumina and/or silica, other suitable support/carrier materials can include, but are not limited to, zeolites, titania, silica-titania, and titania-alumina. Suitable aluminas are porous aluminas such as gamma or eta having average pore sizes from 50 to 200 Å, or 75 to 150 Å; a surface area from 100 to 300 m$^2$/g, or 150 to 250 m$^2$/g; and a pore volume of from 0.25 to 1.0 cm$^3$/g, or 0.35 to 0.8 cm$^3$/g. More generally, any convenient size, shape, and/or pore size distribution for a catalyst suitable for hydrotreatment of a distillate (including lubricant base stock) boiling range feed in a conventional manner may be used. Preferably, the support or carrier material is an amorphous support, such as a refractory oxide. Preferably, the support or carrier material can be free or substantially free of the presence of molecular sieve, where substantially free of molecular sieve is defined as having a content of molecular sieve of less than about 0.01 wt %.

The at least one Group VIII non-noble metal, in oxide form, can typically be present in an amount ranging from about 2 wt % to about 40 wt %, preferably from about 4 wt % to about 15 wt %. The at least one Group VI metal, in oxide form, can typically be present in an amount ranging from about 2 wt % to about 70 wt %, preferably for supported catalysts from about 6 wt % to about 40 wt % or from about 10 wt % to about 30 wt %. These weight percents are based on the total weight of the catalyst. Suitable metal catalysts include cobalt/molybdenum (1-10% Co as oxide, 10-40% Mo as oxide), nickel/molybdenum (1-10% Ni as oxide, 10-40% Co as oxide), or nickel/tungsten (1-10% Ni as oxide, 10-40% W as oxide) on alumina, silica, silica-alumina, or titania.

The hydrotreatment is carried out in the presence of hydrogen. A hydrogen stream is, therefore, fed or injected into a vessel or reaction zone or hydroprocessing zone in which the hydroprocessing catalyst is located. Hydrogen, which is contained in a hydrogen "treat gas," is provided to the reaction zone. Treat gas, as referred to in this invention, can be either pure hydrogen or a hydrogen-containing gas, which is a gas stream containing hydrogen in an amount that is sufficient for the intended reaction(s), optionally including one or more other gasses (e.g., nitrogen and light hydrocarbons such as methane). The treat gas stream introduced into a reaction stage will preferably contain at least about 50 vol. % and more preferably at least about 75 vol. % hydrogen. Optionally, the hydrogen treat gas can be substantially free (less than 1 vol %) of impurities such as H$_2$S and NH$_3$ and/or such impurities can be substantially removed from a treat gas prior to use.

Hydrogen can be supplied at a rate of from about 100 SCF/B (standard cubic feet of hydrogen per barrel of feed) (17 Nm$^3$/m$^3$) to about 10000 SCF/B (1700 Nm$^3$/m$^3$). Preferably, the hydrogen is provided in a range of from about 200 SCF/B (34 Nm$^3$/m$^3$) to about 2500 SCF/B (420 Nm$^3$/m$^3$). Hydrogen can be supplied co-currently with the input feed to the hydrotreatment reactor and/or reaction zone or separately via a separate gas conduit to the hydrotreatment zone.

Hydrotreating conditions can include temperatures of 200° C. to 450° C., or 315° C. to 425° C.; pressures of 250 psig (1.8 MPag) to 5000 psig (34.6 MPag) or 300 psig (2.1 MPag) to 3000 psig (20.8 MPag); liquid hourly space velocities (LHSV) of 0.1 hr$^{-1}$ to 10 hr$^{-1}$; and hydrogen treat rates of 200 scf/B (35.6 m$^3$/m$^3$) to 10,000 scf/B (1781 m$^3$/m$^3$), or 500 (89 m$^3$/m$^3$) to 10,000 scf/B (1781 m$^3$/m$^3$).

Additionally or alternately, the feed can be exposed to a hydrocracking catalyst under effective hydrocracking conditions. Hydrocracking catalysts typically contain sulfided base metals on acidic supports, such as amorphous silica alumina, cracking zeolites such as USY, or acidified alumina. Often these acidic supports are mixed or bound with other metal oxides such as alumina, titania or silica. Examples of suitable acidic supports include acidic molecular sieves, such as zeolites or silicoaluminophosphates. One example of suitable zeolite is USY, such as a USY zeolite with cell size of 24.30 Angstroms or less. Additionally or alternately, the catalyst can be a low acidity molecular sieve, such as a USY zeolite with a Si to Al ratio of at least about 20, and preferably at least about 40 or 50. ZSM-48, such as ZSM-48 with a SiO$_2$ to Al$_2$O$_3$ ratio of about 110 or less, such as about 90 or less, is another example of a potentially suitable hydrocracking catalyst. Still another option is to use a combination of USY and ZSM-48. Still other options include using one or more of zeolite Beta, ZSM-5, ZSM-35, or ZSM-23, either alone or in combination with a USY catalyst. Non-limiting examples of metals for hydrocracking catalysts include metals or combinations of metals that include at least one Group VIII metal, such as nickel, nickel-cobalt-molybdenum, cobalt-molybdenum, nickel-tungsten, nickel-molybdenum, and/or nickel-molybdenum-tungsten. Additionally or alternately, hydrocracking catalysts with noble metals can also be used. Non-limiting examples of noble metal catalysts include those based on platinum and/or palladium. Support materials which may be used for both the noble and non-noble metal catalysts can comprise a refractory oxide material such as alumina, silica, alumina-silica, kieselguhr, diatomaceous earth, magnesia, zirconia, or combinations thereof, with alumina, silica, alumina-silica being the most common (and preferred, in one embodiment).

When only one hydrogenation metal is present on a hydrocracking catalyst, the amount of that hydrogenation metal can be at least about 0.1 wt % based on the total weight of the catalyst, for example at least about 0.5 wt % or at least about 0.6 wt %. Additionally or alternately when only one hydrogenation metal is present, the amount of that hydrogenation metal can be about 5.0 wt % or less based on the total weight of the catalyst, for example about 3.5 wt % or less, about 2.5 wt % or less, about 1.5 wt % or less, about 1.0 wt % or less, about 0.9 wt % or less, about 0.75 wt % or less, or about 0.6 wt % or less. Further additionally or alternately when more than one hydrogenation metal is present, the collective amount of hydrogenation metals can be at least about 0.1 wt % based on the total weight of the catalyst, for example at least about 0.25 wt %, at least about 0.5 wt %, at least about 0.6 wt %, at least about 0.75 wt %, or at least about 1 wt %. Still further additionally or alternately when more than one hydrogenation metal is present, the collective amount of hydrogenation metals can be about 35 wt % or less based on the total weight of the catalyst, for example about 30 wt % or less, about 25 wt % or less, about 20 wt % or less, about 15 wt % or less, about 10 wt % or less, or about 5 wt % or less. In embodiments wherein the supported metal comprises a noble metal, the amount of noble metal(s) is typically less than about 2 wt %, for example less than about 1 wt %, about 0.9 wt % or less, about 0.75 wt % or less, or about 0.6 wt % or less. It is noted that hydrocracking under sour conditions is typically performed using a base metal (or metals) as the hydrogenation metal.

In various aspects, the conditions selected for hydrocracking for lubricant base stock production can depend on the desired level of conversion, the level of contaminants in the input feed to the hydrocracking stage, and potentially other factors. For example, hydrocracking conditions in a single stage, or in the first stage and/or the second stage of a multi-stage system, can be selected to achieve a desired level of conversion in the reaction system. Hydrocracking conditions can be referred to as sour conditions or sweet conditions, depending on the level of sulfur and/or nitrogen present within a feed. For example, a feed with 100 wppm or less of sulfur and 50 wppm or less of nitrogen, preferably less than 25 wppm sulfur and/or less than 10 wppm of nitrogen, represent a feed for hydrocracking under sweet conditions. In various aspects, hydrocracking can be performed on a thermally cracked resid, such as a deasphalted oil derived from a thermally cracked resid. In some aspects, such as aspects where an optional hydrotreating step is used prior to hydrocracking, the thermally cracked resid may correspond to a sweet feed. In other aspects, the thermally cracked resid may represent a feed for hydrocracking under sour conditions.

A hydrocracking process under sour conditions can be carried out at temperatures of about 550° F. (288° C.) to about 840° F. (449° C.), hydrogen partial pressures of from about 1500 psig to about 5000 psig (10.3 MPag to 34.6 MPag), liquid hourly space velocities of from 0.05 $h^{-1}$ to 10 $h^{-1}$, and hydrogen treat gas rates of from 35.6 $m^3/m^3$ to 1781 $m^3/m^3$ (200 SCF/B to 10,000 SCF/B). In other embodiments, the conditions can include temperatures in the range of about 600° F. (343° C.) to about 815° F. (435° C.), hydrogen partial pressures of from about 1500 psig to about 3000 psig (10.3 MPag-20.9 MPag), and hydrogen treat gas rates of from about 213 $m^3/m^3$ to about 1068 $m^3/m^3$ (1200 SCF/B to 6000 SCF/B). The LHSV can be from about 0.25 to about 50 $h^{-1}$, or from about 0.5 to about 20 $h^{-1}$, preferably from about 1.0 to about 4.0 $h^{-1}$.

In some aspects, a portion of the hydrocracking catalyst can be contained in a second reactor stage. In such aspects, a first reaction stage of the hydroprocessing reaction system can include one or more hydrotreating and/or hydrocracking catalysts. The conditions in the first reaction stage can be suitable for reducing the sulfur and/or nitrogen content of the feedstock. A separator can then be used in between the first and second stages of the reaction system to remove gas phase sulfur and nitrogen contaminants. One option for the separator is to simply perform a gas-liquid separation to remove contaminant. Another option is to use a separator such as a flash separator that can perform a separation at a higher temperature. Such a high temperature separator can be used, for example, to separate the feed into a portion boiling below a temperature cut point, such as about 350° F. (177° C.) or about 400° F. (204° C.), and a portion boiling above the temperature cut point. In this type of separation, the naphtha boiling range portion of the effluent from the first reaction stage can also be removed, thus reducing the volume of effluent that is processed in the second or other subsequent stages. Of course, any low boiling contaminants in the effluent from the first stage would also be separated into the portion boiling below the temperature cut point. If sufficient contaminant removal is performed in the first stage, the second stage can be operated as a "sweet" or low contaminant stage.

Still another option can be to use a separator between the first and second stages of the hydroprocessing reaction system that can also perform at least a partial fractionation of the effluent from the first stage. In this type of aspect, the effluent from the first hydroprocessing stage can be separated into at least a portion boiling below the distillate (such as diesel) fuel range, a portion boiling in the distillate fuel range, and a portion boiling above the distillate fuel range. The distillate fuel range can be defined based on a conventional diesel boiling range, such as having a lower end cut point temperature of at least about 350° F. (177° C.) or at least about 400° F. (204° C.) to having an upper end cut point temperature of about 700° F. (371° C.) or less or 650° F. (343° C.) or less. Optionally, the distillate fuel range can be extended to include additional kerosene, such as by selecting a lower end cut point temperature of at least about 300° F. (149° C.).

In aspects where the inter-stage separator is also used to produce a distillate fuel fraction, the portion boiling below the distillate fuel fraction includes, naphtha boiling range molecules, light ends, and contaminants such as $H_2S$. These different products can be separated from each other in any convenient manner. Similarly, one or more distillate fuel fractions can be formed, if desired, from the distillate boiling range fraction. The portion boiling above the distillate fuel range represents the potential lubricant base stocks. In such aspects, the portion boiling above the distillate fuel range is subjected to further hydroprocessing in a second hydroprocessing stage.

A hydrocracking process under sweet conditions can be performed under conditions similar to those used for a sour hydrocracking process, or the conditions can be different. In an embodiment, the conditions in a sweet hydrocracking stage can have less severe conditions than a hydrocracking process in a sour stage. Suitable hydrocracking conditions for a non-sour stage can include, but are not limited to, conditions similar to a first or sour stage. Suitable hydrocracking conditions can include temperatures of about 500° F. (260° C.) to about 840° F. (449° C.), hydrogen partial pressures of from about 1500 psig to about 5000 psig (10.3 MPag to 34.6 MPag), liquid hourly space velocities of from 0.05 $h^{-1}$ to 10 $h^{-1}$, and hydrogen treat gas rates of from 35.6 $m^3/m^3$ to 1781 $m^3/m^3$ (200 SCF/B to 10,000 SCF/B). In other embodiments, the conditions can include temperatures in the range of about 600° F. (343° C.) to about 815° F. (435° C.), hydrogen partial pressures of from about 1500 psig to about 3000 psig (10.3 MPag-20.9 MPag), and hydrogen treat gas rates of from about 213 $m^3/m^3$ to about 1068 $m^3/m^3$ (1200 SCF/B to 6000 SCF/B). The LHSV can be from about 0.25 $h^{-1}$ to about 50 $h^{-1}$, or from about 0.5 $h^{-1}$ to about 20 $h^{-1}$, preferably from about 1.0 $h^{-1}$ to about 4.0 $h^{-1}$.

In still another aspect, the same conditions can be used for hydrotreating and hydrocracking beds or stages, such as using hydrotreating conditions for both or using hydrocracking conditions for both. In yet another embodiment, the pressure for the hydrotreating and hydrocracking beds or stages can be the same.

Before and/or after catalytic dewaxing, the feed (i.e., at least a lubricant boiling range portion thereof) can optionally be exposed to an aromatic saturation catalyst, which can alternatively be referred to as a hydrofinishing catalyst. Exposure to the aromatic saturation catalyst can occur either before or after fractionation. If aromatic saturation occurs after fractionation, the aromatic saturation can be performed on one or more portions of the fractionated product. Alternatively, the entire effluent from the last hydrocracking or dewaxing process can be hydrofinished and/or undergo aromatic saturation.

Hydrofinishing and/or aromatic saturation catalysts can include catalysts containing Group VI metals, Group VIII metals, and mixtures thereof. In an embodiment, preferred metals include at least one metal sulfide having a strong hydrogenation function. In another embodiment, the hydrofinishing catalyst can include a Group VIII noble metal, such as Pt, Pd, or a combination thereof. The mixture of metals may also be present as bulk metal catalysts wherein the amount of metal is about 30 wt. % or greater based on catalyst. For supported hydrotreating catalysts, suitable metal oxide supports include low acidic oxides such as silica, alumina, silica-aluminas or titania, preferably alumina. The preferred hydrofinishing catalysts for aromatic saturation will comprise at least one metal having relatively strong hydrogenation function on a porous support. Typical support materials include amorphous or crystalline oxide materials such as alumina, silica, and silica-alumina. The support materials may also be modified, such as by halogenation, or in particular fluorination. The metal content of the catalyst is often as high as about 20 weight percent for non-noble metals. In an embodiment, a preferred hydrofinishing catalyst can include a crystalline material belonging to the M41S class or family of catalysts. The M41S family of catalysts are mesoporous materials having high silica content. Examples include MCM-41, MCM-48 and MCM-50. A preferred member of this class is MCM-41.

Hydrofinishing conditions can include temperatures from about 125° C. to about 425° C., preferably about 180° C. to about 280° C., a hydrogen partial pressure from about 500 psig (3.4 MPa) to about 3000 psig (20.7 MPa), preferably about 1500 psig (10.3 MPa) to about 2500 psig (17.2 MPa), and liquid hourly space velocity from about 0.1 hr$^{-1}$ to about 5 hr$^{-1}$ LHSV, preferably about 0.5 hr$^{-1}$ to about 1.5 hr$^{-1}$. Additionally, a hydrogen treat gas rate of from 35.6 m$^3$/m$^3$ to 1781 m$^3$/m$^3$ (200 SCF/B to 10,000 SCF/B) can be used.

Bright Stock Products

In various aspects, bright stocks produced using conditions selected and/or modified based on FTICR data can have a kinematic viscosity at 100° C. of 20 cSt or more, or 24 cSt or more, or 30 cSt or more, or 32 cSt or more, such as up to 120 cSt or more. In some aspects, the bright stocks can correspond to bright stocks that contain less than 10 wt % aromatics/greater than 90 wt % saturates and less than 300 wppm sulfur. Optionally, the saturates content can be still higher, such as greater than 95 wt %, or greater than 97 wt %. In other aspects, the aromatics content can be greater than 10 wt %, such as up to 40 wt %, and/or the sulfur content can be greater than 300 wppm, such as up to 10000 wppm or possibly still higher. In some aspects, the bright stock products can have a pour point of 0° C. or less, or −6° C. or less, such as down to −40° C. or possibly still lower. In some aspects, the bright stock can have a residual wax content that corresponds to 50 wt % or less of the wax content of the feedstock prior to dewaxing, or 30 wt % or less, or 20 wt % or less.

The resulting bright stocks can be blended with additives to form formulated lubricants, such as but not limited to marine oils, engine oils, greases, paper machine oils, and gear oils. These additives may include, but are not restricted to, detergents, dispersants, antioxidants, viscosity modifiers, and pour point depressants. More generally, a formulated lubricating including a base stock produced from a deasphalted oil may additionally contain one or more of the other commonly used lubricating oil performance additives including but not limited to antiwear agents, dispersants, other detergents, corrosion inhibitors, rust inhibitors, metal deactivators, extreme pressure additives, anti-seizure agents, wax modifiers, viscosity index improvers, viscosity modifiers, fluid-loss additives, seal compatibility agents, friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. These additives are commonly delivered with varying amounts of diluent oil, that may range from 5 weight percent to 50 weight percent.

When so blended, the performance as measured by standard low temperature tests such as the Mini-Rotary Viscometer (MRV) and Brookfield test has been shown to be superior to formulations blended with traditional base oils.

It has also been found that the oxidation performance, when blended into industrial oils using common additives such as, but not restricted to, defoamants, pour point depressants, antioxidants, rust inhibitors, has exemplified superior oxidation performance in standard oxidation tests such as the US Steel Oxidation test compared to traditional base stocks.

Other performance parameters such as interfacial properties, deposit control, storage stability, and toxicity have also been examined and are similar to or better than traditional base oils.

In addition to being blended with additives, the base stocks described herein can also be blended with other base stocks to make a base oil. These other base stocks include solvent processed base stocks, hydroprocessed base stocks, synthetic base stocks, base stocks derived from Fisher-Tropsch processes, PAO, and naphthenic base stocks. Additionally or alternately, the other base stocks can include Group I base stocks, Group II base stocks, Group III base stocks, Group IV base stocks, and/or Group V base stocks. Additionally or alternately, still other types of base stocks for blending can include hydrocarbyl aromatics, alkylated aromatics, esters (including synthetic and/or renewable esters), and or other non-conventional or unconventional base stocks. These base oil blends of the inventive base stock and other base stocks can also be combined with additives, such as those mentioned above, to make formulated lubricants.

ADDITIONAL EMBODIMENTS

Embodiment 1

A method for forming a bright stock, comprising: performing FTICR on a sample of a feedstock to determine amounts of one or more Z-classes within the feedstock, to determine amounts of one or more homologous series of compounds within the feedstock, or a combination thereof; characterizing waxy components within the sample of the feedstock based on the one or more determined Z-classes, the determined one or more homologous series of compounds, or the combination thereof; selecting at least one processing condition based on the characterization of the waxy components, the at least one processing condition optionally comprising at least one of a pour point, a feed rate, a dewaxing temperature, a solvent to oil ratio, and a dewaxing solvent; and i) performing solvent dewaxing on at least a portion of the feedstock under solvent dewaxing conditions to form a dewaxed oil, the dewaxed oil comprising a bright stock portion having a kinematic viscosity at 100° C. of 20 cSt or more, the solvent dewaxing conditions comprising the at least one of the pour point, the feed rate, the dewaxing temperature, the solvent to oil ratio, and the dewaxing solvent; or ii) performing catalytic dewaxing on at least a portion of the feedstock under catalytic dewaxing conditions to form a dewaxed oil, the catalytic dewaxing conditions comprising the at least one processing condition, the dewaxed oil comprising a bright stock portion having a kinematic viscosity at 100° C. of 20 cSt or more.

Embodiment 2

The method of Embodiment 1, further comprising selecting a filter cake size for the solvent dewaxing conditions.

Embodiment 3

The method of any of the above embodiments, wherein the waxy components are characterized based on a measured amount of compounds in the feedstock having a Z-class of 2 to −60 (or 2 to −20, or 2 to −4).

Embodiment 4

The method of any of the above embodiments, wherein the waxy components are characterized based on a combination of Z-class and molecular weight.

Embodiment 5

The method of Embodiment 1, wherein the waxy components are characterized based on characterization of one or more homologous series of compounds.

Embodiment 6

The method of Embodiment 5, wherein the one or more homologous series of compounds are characterized based on a split of the one or more homologous series of compounds between the dewaxed oil and a wax fraction during the solvent dewaxing.

Embodiment 7

The method of Embodiment 6, wherein characterizing the waxy components further comprises predicting a wax yield for the solvent dewaxing conditions; or wherein characterizing the waxy components further comprises predicting a residual wax content in the dewaxed oil; or a combination thereof.

Embodiment 8

The method of Embodiment 7, further comprising selecting the feedstock for solvent processing based on a target pour point and an amount of residual wax in the dewaxed oil at a residual wax temperature; or wherein selecting a pour point comprises selecting a pour point that corresponds to a predicted residual wax content at a residual wax temperature that is less than 50% of a wax content of the feedstock determined by characterizing the waxy components (or less than 30%, or less than 20%); or a combination thereof.

Embodiment 9

The method of any of Embodiments 1 or 3-5, wherein the at least one processing condition comprises a pour point, or wherein selecting the at least one processing condition comprises selecting a dewaxing catalyst based on the characterized waxy components, or a combination thereof.

Embodiment 10

A method for de-oiling a wax formed during solvent dewaxing, comprising: performing FTICR on a sample of a feedstock to determine amounts of one or more Z-classes within the feedstock, to determine amounts of one or more homologous series of compounds within the feedstock, or a combination thereof; characterizing waxy components within the sample of the feedstock based on the one or more determined Z-classes, the determined one or more homologous series of compounds, or the combination thereof; performing solvent dewaxing on at least a portion of the feedstock under solvent dewaxing conditions to form a dewaxed oil and a wax product, the dewaxed oil comprising a bright stock portion having a kinematic viscosity at 100° C. of 20 cSt or more; selecting at least one of a feed rate, a de-oiling temperature, a solvent to oil ratio, and a dewaxing solvent based on the characterization of the waxy components; and performing solvent de-oiling on the wax product under solvent de-oiling conditions to form de-oiled wax and an oil phase product, the solvent de-oiling conditions comprising the at least one of the feed rate, the de-oiling temperature, the solvent to oil ratio, and the dewaxing solvent.

Embodiment 11

The method of Embodiment 10, wherein the oil phase product has a kinematic viscosity at 100° C. of 12 cSt to 30 cSt.

Embodiment 12

The method of Embodiment 10 or 11, wherein the waxy components are characterized based on a combination of Z-class and molecular weight, or wherein the waxy components are characterized based on characterization of one or more homologous series of compounds, or a combination thereof.

Embodiment 13

The method of Embodiment 12, wherein the one or more homologous series of compounds are characterized based on a split of the one or more homologous series of compounds between the dewaxed oil and a wax fraction during the solvent dewaxing.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for forming a bright stock, comprising:
    performing FTICR on a sample of a feedstock to determine amounts of one or more Z-classes within the feedstock, to determine amounts of one or more homologous series of compounds within the feedstock, or a combination thereof;
    characterizing waxy components within the sample of the feedstock based on the one or more determined Z-classes, the determined one or more homologous series of compounds, or the combination thereof;
    selecting at least one of a feed rate, a dewaxing temperature, a solvent to oil ratio, and a dewaxing solvent based on the characterization of the waxy components; and
    performing solvent dewaxing on at least a portion of the feedstock under solvent dewaxing conditions to form a dewaxed oil, the dewaxed oil comprising a bright stock portion having a kinematic viscosity at 100° C. of 20 cSt or more, the solvent dewaxing conditions comprising the at least one of, the feed rate, the dewaxing temperature, the solvent to oil ratio, and the dewaxing solvent.

2. The method of claim 1, further comprising selecting a filter cake size for the solvent dewaxing conditions.

3. The method of claim 1, wherein the waxy components are characterized based on a measured amount of compounds in the feedstock having a Z-class of 2 to −60 (or 2 to −20, or 2 to −4).

4. The method of claim 1, wherein the waxy components are characterized based on a combination of Z-class and molecular weight.

5. The method of claim 1, wherein the waxy components are characterized based on characterization of one or more homologous series of compounds.

6. The method of claim 5, wherein the one or more homologous series of compounds are characterized based on a split of the one or more homologous series of compounds between the dewaxed oil and a wax fraction during the solvent dewaxing.

7. The method of claim 6, wherein characterizing the waxy components further comprises predicting a wax yield for the solvent dewaxing conditions.

8. The method of claim 6, wherein characterizing the waxy components further comprises predicting a residual wax content in the dewaxed oil.

9. The method of claim 6, further comprising selecting the feedstock for solvent processing based on a target pour point and an amount of residual wax in the dewaxed oil at a residual wax temperature.

10. A method for forming a bright stock, comprising:
    performing FTICR on a sample of a feedstock to determine amounts of one or more Z-classes within the feedstock, to determine amounts of one or more homologous series of compounds within the feedstock, or a combination thereof;
    characterizing waxy components within the feedstock based on the one or more determined Z-classes, the determined one or more homologous series of compounds, or the combination thereof;
    selecting at least one processing condition based on the characterization of the waxy components; and
    performing catalytic dewaxing on at least a portion of the feedstock under catalytic dewaxing conditions to form a dewaxed oil, the catalytic dewaxing conditions comprising the at least one processing condition, the dewaxed oil comprising a bright stock portion having a kinematic viscosity at 100° C. of 20 cSt or more.

11. The method of claim 10, wherein selecting the at least one processing condition comprises selecting a dewaxing catalyst based on the characterized waxy components.

12. The method of claim 10, wherein the waxy components are characterized based on a measured amount of compounds in the feedstock having a Z-class of 2 to −60 (or 2 to −20, or 2 to −4).

13. The method of claim 10, wherein characterizing the waxy components further comprises predicting a residual wax content in the dewaxed oil at a residual wax temperature.

14. A method for de-oiling a wax formed during solvent dewaxing, comprising:
    performing FTICR on a sample of a feedstock to determine amounts of one or more Z-classes within the feedstock, to determine amounts of one or more homologous series of compounds within the feedstock, or a combination thereof;
    characterizing waxy components within the sample of the feedstock based on the one or more determined Z-classes, the determined one or more homologous series of compounds, or the combination thereof;
    performing solvent dewaxing on at least a portion of the feedstock under solvent dewaxing conditions to form a dewaxed oil and a wax product, the dewaxed oil comprising a bright stock portion having a kinematic viscosity at 100° C. of 20 cSt or more;
    selecting at least one of a feed rate, a de-oiling temperature, a solvent to oil ratio, and a dewaxing solvent based on the characterization of the waxy components; and
    performing solvent de-oiling on the wax product under solvent de-oiling conditions to form de-oiled wax and an oil phase product, the solvent de-oiling conditions comprising the at least one of the feed rate, the de-oiling temperature, the solvent to oil ratio, and the dewaxing solvent.

15. The method of claim 14, wherein the oil phase product has a kinematic viscosity at 100° C. of 12 cSt to 30 cSt.

16. The method of claim 14, wherein the waxy components are characterized based on a combination of Z-class and molecular weight.

17. The method of claim 14, wherein the waxy components are characterized based on characterization of one or more homologous series of compounds.

18. The method of claim 17, wherein the one or more homologous series of compounds are characterized based on a split of the one or more homologous series of compounds between the dewaxed oil and a wax fraction during the solvent dewaxing.

* * * * *